US006221651B1

(12) United States Patent
Kilbane, II et al.

(10) Patent No.: US 6,221,651 B1
(45) Date of Patent: Apr. 24, 2001

(54) *PSEUDOMONAS AYUCIDA* USEFUL FOR CLEAVAGE OF ORGANIC C-N BONDS

(75) Inventors: John J. Kilbane, II, Woodstock, IL (US); Claudia Marie Soares Ribeiro; Mônica Moreira Linhares, both of Rio de Janeiro (BR)

(73) Assignee: Petroleo Brasileiro S.A.-Petrobras, Rio de Janeiro (BR)

( * ) Notice: Subject to any disclaimer, the term of this patent is extended or adjusted under 35 U.S.C. 154(b) by 0 days.

(21) Appl. No.: 09/564,642

(22) Filed: May 3, 2000

Related U.S. Application Data

(62) Division of application No. 09/449,615, filed on Nov. 30, 1999.

(51) Int. Cl.[7] ............................... C12N 1/20; C12N 1/00; C10G 32/00; B01D 1/00; C02F 3/00
(52) U.S. Cl. ..................... 435/253.3; 435/281; 435/874; 210/600; 210/610
(58) Field of Search ............................... 435/253.3, 281, 435/874

(56) References Cited

U.S. PATENT DOCUMENTS

| 5,002,888 | 3/1991 | Kilbane, II et al. ............ 435/252.31 |
| 5,143,827 | * 9/1992 | Atlas et al. . |
| 5,297,625 | 3/1994 | Premuzic et al. ................... 166/246 |

OTHER PUBLICATIONS

Wakabayashi et al. Fish Pathology, 31(4), 239–240. Bacterial hemorrhagic ascites of ayu caused by Pseudomonas sp., Dec. 1996.*

The American Type Culture Collection. Internet http://phage.atcc.org.*

Shukla, Onkar P., "Microbial Transformation of Quinoline by a Pseudomonas sp.", Applied and Environmental Microbiology, vol 51, Jun. 1986, pp. 1332–1342.

Schwarz, G. et al., "Microbial Metabolism of Quinoline and Related Compounds. I. Isolation and Characterization of Quinoline–Degrading Bacteria", System Appl. Microbiol. 10, 185–190 (1998).

Grant, D.J.W. et al., "Degradation of quinoline by a soil bacterium", Microbios 1976, 15, pp. 177–189.

O'Loughlin, E.J. et al, "Isolation, Characterization and Substrate Utilization of a Quinoline–Degrading Bacterium", International Biodeterioration and Biodegradation (1996), pp. 107–118.

Asilabie et al, (1990), "Microbial Degradation of Quinoline and Methylquinoline", Appl. Environ. Microbiol. 56: 345–351.

* cited by examiner

Primary Examiner—Leon B. Lankford, Jr.
Assistant Examiner—Michele C. Flood
(74) Attorney, Agent, or Firm—Sughrue, Mion, Zinn, Macpeak & Seas, PLLC

(57) ABSTRACT

A mutant *Pseudomonas ayucida* strain ATCC N° PTA-806 which is able to selectively cleave organic C—N bonds and reduce the nitrogen content of organic carbonaceous materials is described.

2 Claims, 3 Drawing Sheets

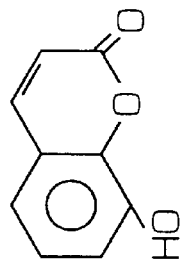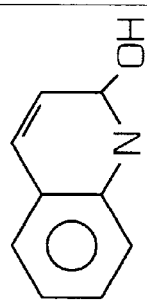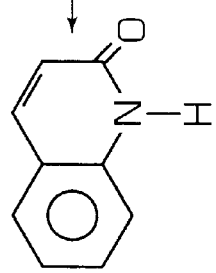
FIG. 3
8-HYDROXYCOUMARIN
2-QUINOLINONE
QUINOLINE

PSEUDOMONAS AYUCIDA USEFUL FOR CLEAVAGE OF ORGANIC C-N BONDS

This application is a Div of Ser. No. 09/449,615 filed Nov. 30, 1999.

FIELD OF THE INVENTION

This invention relates to a mutant culture of *Pseudomonas ayucida* capable of selective removal of organically bound nitrogen from carbonaceous materials while maintaining the calorific value of the carbonaceous materials. The microorganisms of this invention are particularly useful in removal of organic nitrogen from fossil fuels such as nitrogen-containing coal and oils.

BACKGROUND INFORMATION

The quality of petroleum is progressively deteriorating as the highest quality petroleum deposits are preferentially produced. Consequently, the concern about the concentration of compounds/contaminants such as sulfur, nitrogen, and metals in petroleum will intensify. These contaminants are not only contributors to environmental pollution resulting from the combustion of petroleum, but also interfere with the processing of petroleum by poisoning catalysts and contributing to corrosion. Further, the presence of these contaminants lowers the price of the oil and related products. The selective removal of contaminants from petroleum while retaining the fuel value is a difficult technical challenge.

The selective removal of sulfur from dibenzothiophene with the aid of a bacterium useful for cleaving C—S bonds is taught in U.S. Pat. No. 5,002,888.

U.S. Pat. No. 5,297,625 teaches a method for preparing, isolating and utilizing a microorganism which can metabolize crude oils and other high molecular weight hydrocarbons as a source of energy, and emulsify heavy crudes under the extreme conditions existing in oil reservoirs.

Biorefining of petroleum is therefore a technology soon being commercialized and which may be very promising.

The removal of nitrogen and metals from petroleum is a further potential use of biocatalysts, but so far this area of research has received very little attention.

Quinoline is perhaps the most widely, studied organonitrogen compound as regards biodegradation, and quinoline is considered to be representative of many organonitrogen compounds typically found in petroleum. Many aerobic and anaerobic microbial cultures have been found that can degrade quinoline. The majority, if not the entirety, of microbial cultures described in the literature that metabolize quinoline do so by fully degrading it, and can therefore utilize quinoline as a sole source of carbon, energy, and nitrogen.

Shukla, Onkar P., in "Microbial Transformation of Quinoline by a Pseudomonas sp.", Applied and Environmental Microbiology, vol 51, June 1986, p. 1332–1342, reports that a Pseudomonas sp isolated from sewage by enrichment culture on quinoline metabolized this substrate by a novel pathway involving 8-hydroxycoumarin. Such microorganism utilizes quinoline as the sole source of carbon, nitrogen, and energy.

Schwarz, G. et al, in "Microbial Metabolism of Quinoline and Related Compounds. I. Isolation and Characterization of Quinoline-Degrading Bacteria", System. Appl. Microbiol. 10, 185–190 (1988) report that from soil, water and activated sludge 16 bacterial strains were isolated which are able to use quinoline as sole source of carbon and nitrogen. Of the 16 bacterial strains investigated, 13 could be allocated to the genus Pseudomonas. These bacteria are Gram-negative, straight to slightly curved, motile rods, which on HNB-agar form yellowish to cream-colored, circular, smooth or partially rough colonies. The species were identified as *Pseudomonas putida* Biovars A and B, *Pseudomonas fluorescens* and *Pseudomonas testosteroni*. It is reported that growth on 2-hydroxyquinoline is common to all strains, which were investigated. With several Pseudomonas species the degradation of quinoline has been studied and 2-hydroxyquinoline was found to be the first intermediate in the degradation pathway.

Grant, D. J. W. et al. In "Degradation of quinoline by a soil bacterium", Microbios 1976, 15, p. 177–189, report that from garden soil a bacterium was isolated which grew aerobically in mineral salts medium with quinoline as sole C source and $NH_4^+$ as N source. During growth with quinoline, 2-hydroxyquinoline accumulated in the culture fluid and later disappeared. 2,6-Dihydroxyquinoline is probably the next intermediate since whole cells oxidize it rapidly and completely. Aromatic ring cleavage under aerobic conditions almost invariably follows the formation of a compound with two hydroxyl groups attached to a ring in positions o- or p- to each other.

O'Loughlin, E. J. et al. In "Isolation, Characterization and Substrate Utilization of a Quinoline-Degrading Bacterium", International Biodeterioration and Biodegradation (1996), 107–118 report a Gram (+) rod-shaped organism identified as a Rhodococcus sp. capable of growth utilizing quinoline as the dominant carbon, energy, and nitrogen source. The isolate, designated as Rhodococcus sp. Q1 was also capable of growth on 2-hydroxyquinoline, pyridine, 2,3-dimethyl pyridine, catechol, benzoate, and protocatechuic acid, suggesting a diverse capacity for aromatic ring degradation. Although ring nitrogen was released into the growth medium as ammonium, quinoline degradation was not limited by the availability of inorganic N. A degradation product identified as 2-hydroxyquinoline was identified on the basis of several spectroscopic analyses.

Thus, although the cited literature mentions microbial cultures able to metabolize quinoline by fully degrading it, the use of such cultures in a petroleum biodenitrogenation application would require that nitrogen be selectively removed from quinoline leaving the carbon and the calorific value of the molecule intact.

As related in the literature, the metabolic pathways utilized by various aerobic quinoline-degrading microorganisms were shown to initiate the degradation of quinoline by oxidizing and removing nitrogen from quinoline. As no other source of carbon was provided, the metabolism of such species would proceed by cleaving C—C bonds.

While the biodegradation of quinoline has been reasonably well studied there is very little information concerning the use of quinoline-degrading microorganisms to remove nitrogen from petroleum. On the other hand, several quinoline-degrading Pseudomonas were found to have no ability to remove significant levels of nitrogen from crude oil or asphaltene fractions of petroleum. (Aislabie et al. 1990, "Microbial Degradation of Quinoline and Methylquinoline", Appl. Environ. Microbiol. 56: 345–351).

Therefore there is the need to isolate aerobic microbial cultures capable of utilizing quinoline as a nitrogen source, but incapable of utilizing quinoline as a carbon source, then examining the metabolic pathway of quinoline degradation as well as the ability of such cultures to selectively remove nitrogen from petroleum, these goals being achieved by the present invention.

SUMMARY OF THE INVENTION

It is an object of this invention to provide a microorganism and a process for removal of organically bound nitrogen from nitrogen-containing organic carbonaceous materials.

It is another object of this invention to provide a microorganism and process for selective nitrogen removal from organic nitrogen-containing fossil and fossil derived fuels.

It is yet another object of the present invention to provide a microorganism and process capable of specific cleavage or formation of C—N bonds in reactions of organic carbonaceous materials, such as in organic synthesis.

It is yet another object of this invention to provide a microorganism, which is stable and retains its nitrogen specific characteristics under process conditions using the microorganism for cleavage of organic C—N bonding.

It is another object of this invention to provide a microorganism and process for specific nitrogen removal from quinoline resulting in substantially sole products of 2-quinolinone and 8-hydroxycoumarin.

The above and other objects and other advantages, as will become evident from reading of this description, have been achieved by the pure culture of a microorganism which has been isolated and subjected to processes as set forth in further detail in the present specification and identified as *Pseudomonas ayucida*. The culture has been deposited with American Type Culture Collection, 10801 University Blvd Manassas, Va. 20110-2209, U.S.A and assigned ATCC N° PTA-806 PTA-806.

*Pseudomonas ayucida* ATCC N° PTA-806 PTA-806 may be prepared by inoculating samples derived from sites having present materials of C—N bonding desired to be cleaved, a growth medium comprising mineral nutrients, an assimilable source of carbon, and in substantial absence of a nitrogen-containing compound, except compounds having nitrogen present only in C—N bonding of the type desired to be cleaved; growing the bacterial culture in the presence of oxygen at temperatures about 30° C. for sufficient time to selectively produce *Pseudomonas ayucida* ATCC N° PTA-806 which has the property of selective cleavage of C—N bonds in organic carbonaceous materials.

Nitrogen content of nitrogen-containing organic carbonaceous materials may be reduced by contacting such nitrogen-containing organic carbonaceous material with the microorganism *Pseudomonas ayucida* strain ATCC N° PTA-806. The process is especially suitable for use where the nitrogen-containing carbonaceous material is shale oil or hydrocarbon oil. Continuous growth of *Pseudomonas ayucida* strain ATCC N° PTA-806 in the presence of nitrogen-containing shale oil results in the removal of more than 5% total nitrogen and preferably more than 68% of the total quinoline. The process for reducing the nitrogen content of the nitrogen-containing organic carbonaceous material occurs by cleavage of organic C—N bonds by the microorganism *Pseudomonas ayucida* strain ATCC N° PTA-806. The organic nitrogen selective pure culture of *Pseudomonas ayucida* strain ATCC N° PTA-806 has the ability to selectively reduce the nitrogen content of nitrogen-containing organic carbonaceous material by cleavage of organic C—N bonds by production of 2-hydroxyquinoline and 8-hydroxycoumarin when grown in a growth medium comprising mineral nutrients and an assimilable source of carbon in the substantial absence of a nitrogen-containing compound except the nitrogen-containing organic carbonaceous material, and in the presence of oxygen at temperatures about 35° C. to about 30° C. Derivatives of *Pseudomonas ayucida* strain ATCC N° PTA-806 retain the ability to selectively reduce the nitrogen content of nitrogen-containing organic carbonaceous materials by cleavage of organic C—N bonds in the same fashion.

BRIEF DESCRIPTION OF THE DRAWINGS

FIG. 3 is a schematic representation of the partial pathway for the degradation of quinoline by *Pseudomonas ayucida* ATCC N° PTA-806.

DETAILED DESCRIPTION OF THE PREFERRED MODES

Figure 1:
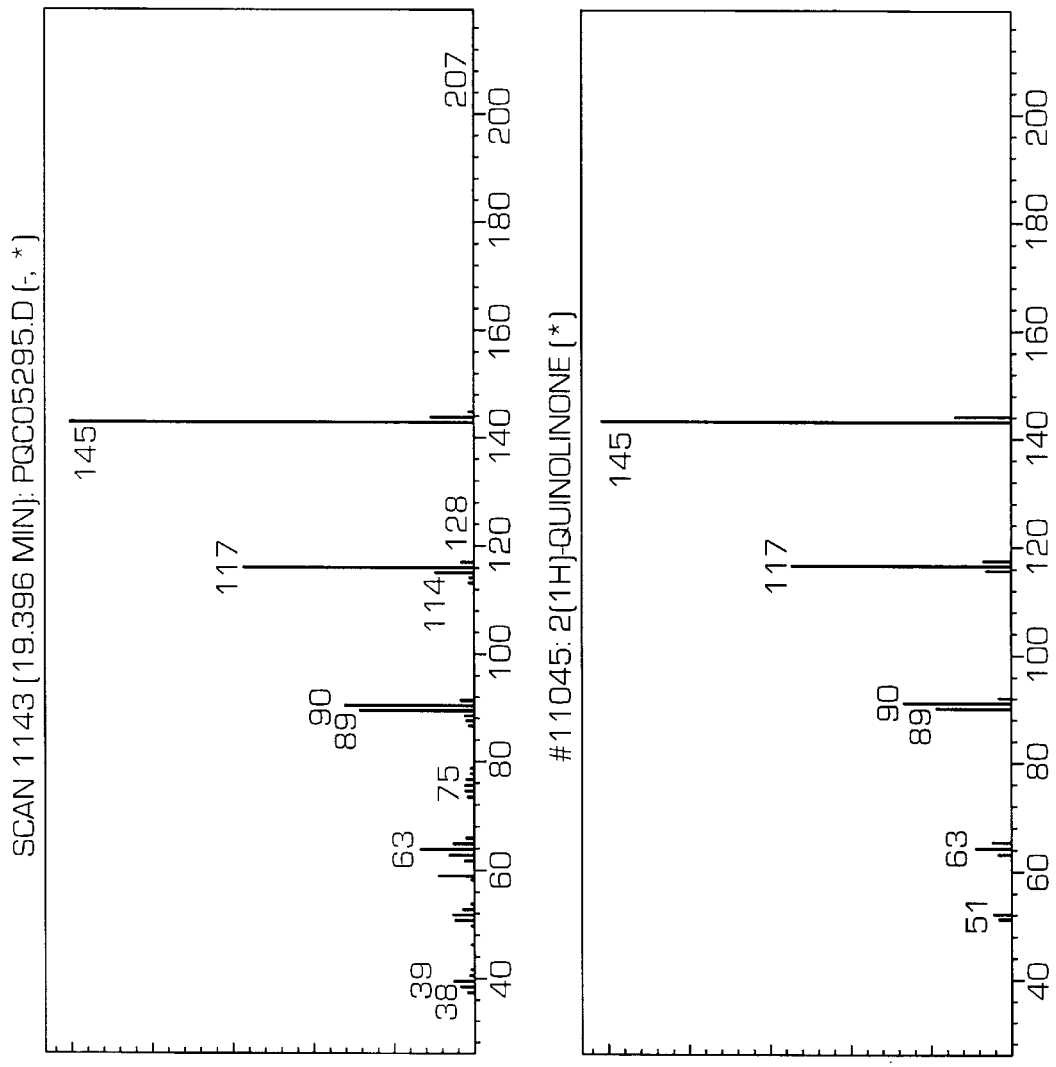
FIG. 1 is a graph which illustrates a comparison of MS data of a metabolite of quinoline produced by *Pseudomonas ayucida* ATCC N° PTA-806 with 2-quinolinone.

Environmental cultures having a known history of exposure to organonitrogen compounds as well as enrichment cultures using as carbon sources acetate, benzene, benzoic acid, ethanol, glucose, glycerol, nutrient broth, succinate, and toluene and organic nitrogen compounds such as quinoline, carbazole and pyridine produce bacterial cultures capable of metabolizing each of the organic nitrogen compounds used. All of the environmental isolates and enrichment cultures tested are reported in the literature to metabolize organonitrogen compounds by initiating biodegradation of the carbon-carbon bond and/or by utilizing the organonitrogen compound as a carbon and energy source.

According to the technical literature, the most widely-known microorganisms for nitrogen utilization from organonitrogen compounds are Pseudomonas isolated from enrichment cultures employing quinoline as the sole source of nitrogen. These Pseudomonas species while capable of utilizing organically bound nitrogen fails to show specificity for the oxidation of carbon-nitrogen bonds. This shows the failure of enrichment culture development of a naturally occurring microorganism showing specificity for oxidation of organic C—N bonds. Thus, an unnatural, selective mutation process must be utilized to develop a microorganism having such selective nitrogen metabolism.

Microorganisms having nitrogen-specific metabolic abilities with respect to organic substrates may be developed by selection through chemostat inoculation and shake flask enrichment culture experiments in which nutrients and organically bound nitrogen not normally found in living tissue may be supplied in the substantial absence of other available nitrogen source such as inorganic nitrogen as $(NH_4)_2SO_4$.

The growth media should supply organic and inorganic nutrients for good microorganism growth, but be devoid of inorganic and other organic nitrogen-containing compounds desired to be metabolized by the microorganism. A suitable media for growth of microorganisms under organonitrogen conditions may suitably be a composition or mineral nutrients, such as 0.37 g $KH_2PO_4$, 0.25 g $MgSO_4.7H_2O$, 0.07 g $CaCl_2.2H_2O$, 0.02 g $FeCl_3$ and 20.0 g of glucose/glycerol/succinate per liter of distilled, deionized water. Such medium is known as ModA. Any assimilable carbon source devoid of nitrogen may be used in amounts to support desired microbial growth. Suitable assimilable carbon sources include glucose, glycerol,. sodium acetate, sodium benzoate, sodium succinate, and sucrose at concentrations of from 1 to 20 mM.

The preferred organonitrogen compound having organic C—N bonds is quinoline. Other suitable compounds having organic C—N bonds are listed hereinbelow.

Environmental samples of soil and/or water may be obtained from petroleum and coal processing sites, compost and other sites where contamination with petroleum hydrocarbons exists.

The environmental samples are used to inoculate chemostat and shake flask enrichment culture experiments to obtain cultures capable of using quinoline as a sole source of nitrogen. In the present invention, all experiments employed the above-defined mineral salt media:

0.37 g $KH_2PO_4$
0.25 g $MgSO_4.7H_2O$
0.07 g $CaCl_2.2H_2O$
0.02 g $FeCl_3$ and 20.0 g of glucose/glycerol/succinate per liter of distilled, deionized water.

This media is adjusted to a pH of 6.5 to 7.0 and nitrogen is supplied in the form of quinoline which is present at concentrations ranging from 1 to 20 mM, or for control experiments $(NH_4)_2SO_4$ is used at a concentration of 1.3 g per liter.

Chemostats and shake flasks are operated at room temperature (25° C.) or 30° C. The working volume of chemostats is one liter and shake flask experiments generally utilize 50 or 100 ml of liquid media. Flow rates of the chemostats are adjusted to achieve hydraulic retention times ranging from two days to as long as a month and the flow rates as well as the organonitrogen test compound are altered as needed to ensure that the chemostats create an environment suitable for the selection of cultures with improved abilities to selectively cleave C—N bonds. The bacterial cell density in the chemostats/shake flasks ranges from $10^2$ to $10^8$ cells/ml, with average cell densities of $10^4$ to $10^5$ cells/ml being maintained. The bacteria isolated from the effluent of chemostats and/or from shake flasks are subjected to chemical mutagenenesis and/or physical mutagenesis using nitrosoguanidine (NTG) and short wave ultraviolet (UV) irradiation respectively. Cell populations are mutagenized under conditions, which result in the death of about 99% of the population. The mutagenized cells are then used to reinoculate chemostats, start additional shake flask experiments, and to streak onto agar plates containing organonitrogen test compounds. Care should be taken to insure that the amount of biomass that is added back to chemostats in the form of inocula is insufficient to provide a significant amount of nitrogen in the form of dead biomass. Cells from the effluents of chemostats, shake flasks, and agar plates are routinely tested using the Nitrogen Bioavailability Test Assay described below.

The determination of 16S-rRNA gene sequences for the determination of the species of bacterial isolates was performed by MIDI Labs (Newark, Del.).

Nitrogen Bioavailability Assay

The ability of bacteria to utilize organic nitrogen compounds for growth can be measured by the Nitrogen Bioavailability Assay (NBA). This assay is based on the fact that all life requires some nitrogen for growth and, therefore, a situation can be created whereby quantifying bacterial growth provides a measure of the utilization of any organic or inorganic compound as a source of nitrogen.

Thus, the Nitrogen Availability Assay utilizes defined mineral salts medium in growth tests in which organonitrogen model compounds such as quinoline, pyridine, carbazole, and porphyrin serve as sources of carbon and/or nitrogen. Growth tests are performed using six conditions:

1. Test compound as sole source of carbon and nitrogen;
2. Test compound as sole source of carbon (alternative nitrogen source, ammonia, is available);
3. Test compound as sole source of nitrogen (alternative carbon source, glucose/glycerol/succinate, is available);
4. Test compound present as well as alternative sources of carbon and nitrogen;
5. Only alternative nitrogen (ammonia) and carbon (glucose/glycerol/succinate) sources are available. The test compound is not present.
6. No nitrogen compounds of any kind are present, but alternative carbon (glucose/glycerol/succinate) sources are available.

These six growth conditions constitute a bioassay for the ability of a culture to metabolize organonitrogen compounds. When carbon and nitrogen sources other than the test compounds are needed, they are supplied in the form of a glucose/glycerol/succinate mixture (20 g/L) and as ammonia (20 mM) respectively.

The NBA test may be performed with any organonitrogen test compound which is ordinarily used at a concentration of from 3 mM to 20 mM.

In order to determine the range of organonitrogen compounds that could serve as sole sources of nitrogen for growth for the various pure cultures of the invention various organonitrogen compounds and control compounds are tested according to the Nitrogen Bioavailability Assay procedure. All compounds are highly pure, analytical grade compounds.

These compounds included:

2-Methyl-beta-Naphthothiazole;
2-Methyl Benzothiazole;
2(Methylmercapto)Benzimidazole;
1,1-Methylene Bis (3-Methyl Pipridine);
Thiazole;
1-Butylpyrrolidine;
2-Methylene-1,3,3-Trimethyl Indoline;
2-Methyl-3-Propylpyrazine;
2-Phenylbenzothiazole;
2-Methyl Quinoxaline;
2-Methyl Indoline;
Carbazole;
Quinoline;
Quinazoline;
Qinoxaline;
2,4-Quinolindiol;
Isoquinoline;
3-Methyl Isoquinoline;
Isocarbostyril;
Protoporphyrin;
Pyridine;
Phenyl Benzothiazole;
Nicotinic Acid;
Imidazole;
Indole;
HEPES Buffer;
Urea;

Guanine;
Lysine;
Tryptophan;
Ammonium Chloride.

The various cultures are inoculated into test tubes or shake flasks containing media components appropriate for the six test conditions.

The cultures are then incubated aerobically for 2 to 4 days, at room temperature or at 30° C.

The growth of the cultures is monitored by measuring the turbidity/optical density of the cultures in the various test conditions, or by determining colony forming units.

Test condition n°6 (nitrogen-free sample) is a negative control.

Test conditions n° 4 and 5 are positive controls since the samples are amended with both a carbon and nitrogen source and therefore should produce healthy microbial growth unless the test compound is toxic to the culture being tested. In this event only condition n° 5 should result in healthy growth.

The amount of bacterial growth observed in test conditions 1, 2 and 3 as compared with the amount of growth observed in test conditions 4, 5 and 6 indicate the ability of cultures to use the organonitrogen test compound as a source of carbon and/or nitrogen.

Cultures which show better growth in test condition n° 3 than in test conditions 1 and 2 may be preferentially utilizing the organonitrogen compound as a nitrogen source only.

Identification of Metabolites

In order to identify metabolites, Thin Layer Chromatography (TLC) is performed on Silica C-18 plates by the method described by G. K. Watson and R. B. Cain in "Microbial metabolism of the Pyridine Ring", Biochem. J. 146:146–172. Running phase solvents are for example hexane, acetic acid and xylene in the ratio of 5:1:2. Supernatants from bacterial cultures grown with quinoline as the sole source of nitrogen are extracted with ethyl acetate and run on TLC plates.

Alternatively, resting cells may be used, employing washed cell pellets derived from log phase cultures grown with either quinoline or ammonia as nitrogen sources. Concentrated cell suspensions are incubated with 20 mM quinoline for periods ranging from 15 minutes to 16 hours.

Extraction of the supernatants from resting cells as well as growing cells may be carried out either by ethyl acetate solvent extraction or with C18 solid phase extraction cartridges and the extracts analyzed by TLC.

Derivation of Metabolites

Derivation of metabolites may be effected by adding semicarbazide-HCl and 2,4 dinitrophenyl hydrazine (2,4-DNPH) to some experiments followed by subsequent extraction and TLC analysis. A typical incubation mixture which utilizes metabolite derivation consists of 200 ml of Medium A (with carbon source) which contains 2 g of cells dry weight, 2 mM semicarbazide-HCl, and 3 mM to 20 mM quinoline as the nitrogen source. The mixture is incubated for 2 hours and the cells are centrifuged. To the supernatant 2,4 DNPH is added, the mixture is left overnight and extracted with ethyl acetate, then separated on a TLC plate and the spots identified.

Gas Chromatography/Mass Spectrometry

GC/MS analysis is performed on extracts derived from growing and resting cell cultures exposed to quinoline, and on compounds eluted from spots observed on TLC plates.

Extraction of the supernatants from resting cells as well as growing cells may be carried out either by ethyl acetate solvent extraction or with C-18 solid phase extraction cartridges. TLC spots of possible metabolites are analyzed by GC/MS.

Mass spectrographs are compared with various libraries of mass spectrograph data prepared from known standard compounds.

Assessment of the ability of *Pseudomonas ayucida* ATCC N° PTA-806 in the cleavage of organic C—N bonds In order to assess the ability of *Pseudomonas ayucida* ATCC N° PTA-806 of cleaving organic C—N bonds, this microorganism is made to grow in ModA medium using quinoline as the sole nitrogen source. One liter of culture OD600=1.67 is produced, which is harvested and the cell pellet is resuspended in 100 ml of ModA medium. The culture is divided into two 50 ml portions and 3 ml of shale oil (1.7 weight % nitrogen) is added to each. Then, the cultures are incubated under agitation at room temperature overnight (16 hours), the oil is separated and analyzed. The amount of quinoline present in oil samples is determined by GC, the area under the peak being corresponding to a retention time for quinoline.

Preparation of a pure culture of mutant *Pseudomonas ayucida* strain ATCC N° PTA-806.

The preparation of a pure culture of a microorganism capable of organic C—N cleavage while maintaining the calorific value of the organic molecule according to the present invention comprises collecting environmental samples obtained from petroleum-contaminated locations, inoculating chemostats and effecting shake flask enrichment culture experiments in which 3 mM to 20 mM quinoline is supplied as the sole source of nitrogen. After the initial period of toxicity of quinoline, bacterial growth yields mixed and pure cultures which are tested using the Nitrogen Bioavailability Assay to detect cultures capable of using quinoline as a nitrogen source, but not as a carbon source.

Quinoline-utilizing cultures initially obtained from the chemostats are found to fully degrade quinoline, utilizing it as a carbon as well as a nitrogen source. Then, the flow rates of the chemostats are increased so as to decrease the hydraulic retention times from 96 hours to 4 hours. Cells from the chemostat effluent are mutagenized and returned to the chemostat. Eventually a pure culture is obtained that yielded Nitrogen Bioavailability Assay results that indicated that quinoline was used as a nitrogen, but not as a carbon source. A partial sequence of the 16S-rRNA gene of this gram negative, rod-shaped bacteria was determined identifying it as *Pseudomonas ayucida* which was deposited in the ATCC under N° PTA-806. *P. monteilii*, which shows 99% homology, and *Pseudomonas nitroreducens* and *Pseudomonas pseudoalcaligenes pesudoalcaligenes*, which both show 98.3% homology, are closely related, but not identical to *Pseudomonas ayucida* PTA-806. Naturally occurring strains of *Pseudomonas ayucida* are not known to be capable of selectively cleaving C—N bonds in quinoline, utilizing quinoline as a nitrogen but not a carbon source. Therefore the culture isolated here and the subject of this patent is unique and is a mutant of *Pseudomonas ayucida* that was intentionally produced in the laboratory by the enrichment culture/directed evolution experiments performed by the Applicant.

*Pseudomonas ayucida* ATCC N° PTA-806 has a cell doubling time of 4.25 hours when grown in defined salts medium at 30° C. with quinoline serving as the sole nitrogen source.

Substrate range and specificity tests are also carried out for the microorganism of the invention, using inocula derived from all of those organonitrogen compounds cited hereinbefore that did yield growth in a previous Nitrogen Bioavailability Assay.

*Pseudomonas ayucida* ATCC N° PTA-806 is found to grow on urea, tryptophan, lysine, guanine, nicotinic acid, quinoline, 3,4-dihydro-(1H)-quinolinone, 2,4-quinolinediol, 8-hydroxyquinoline, and quinoxaline as sole nitrogen sources, but none of these compounds serve as carbon sources.

It should be noted that growth with urea, tryptophan, lysine, guanine and nicotinic acid as nitrogen sources is a common ability possessed by a large number of aerobic bacteria and most likely has no relationship to metabolic pathways relevant to the utilization of quinoline.

The culture grew in the presence of all of the test compounds except 1-butylpyrrolidine and 2-methylene-1,3,3-trimethyl indoline when quinoline was simultaneously present as an alternate nitrogen source.

TLC was performed on the extracts derived from the culture supernatants of *Pseudomonas ayucida* ATCC N° PTA-806 grown with quinoline as sole nitrogen source, as well as pre-grown cells incubated for various times in the presence of quinoline as described hereinbefore. Controls of the culture grown using ammonia rather than quinoline as a nitrogen source were included in all experiments. Additionally, pure chemicals that are possible metabolites of quinoline such as protocatachuate, catechol, pyruvic acid and p-hydroxy benzoic acid, formamide, 8-hydroxyquinoline and succinic acid dimethyl ester were included as standards in TLC experiments to see if these compounds were formed during the microbial degradation of quinoline. Two spots having Retardation factors (Rf) values of 0.73 and 0.88 were identified as possible metabolites of quinoline by *Pseudomonas ayucida* ATCC N° PTA-806 as these compounds were found only in samples derived from the incubation of *Pseudomonas ayucida* ATCC N° PTA-806 with quinoline. Cells of the same culture incubated with ammonia did not produce these compounds. TLC alone could not accurately identify these two compounds so the spots were scraped from TLC plates, eluted with ethyl acetate and subjected to GC/MS analysis.

Figure 2:
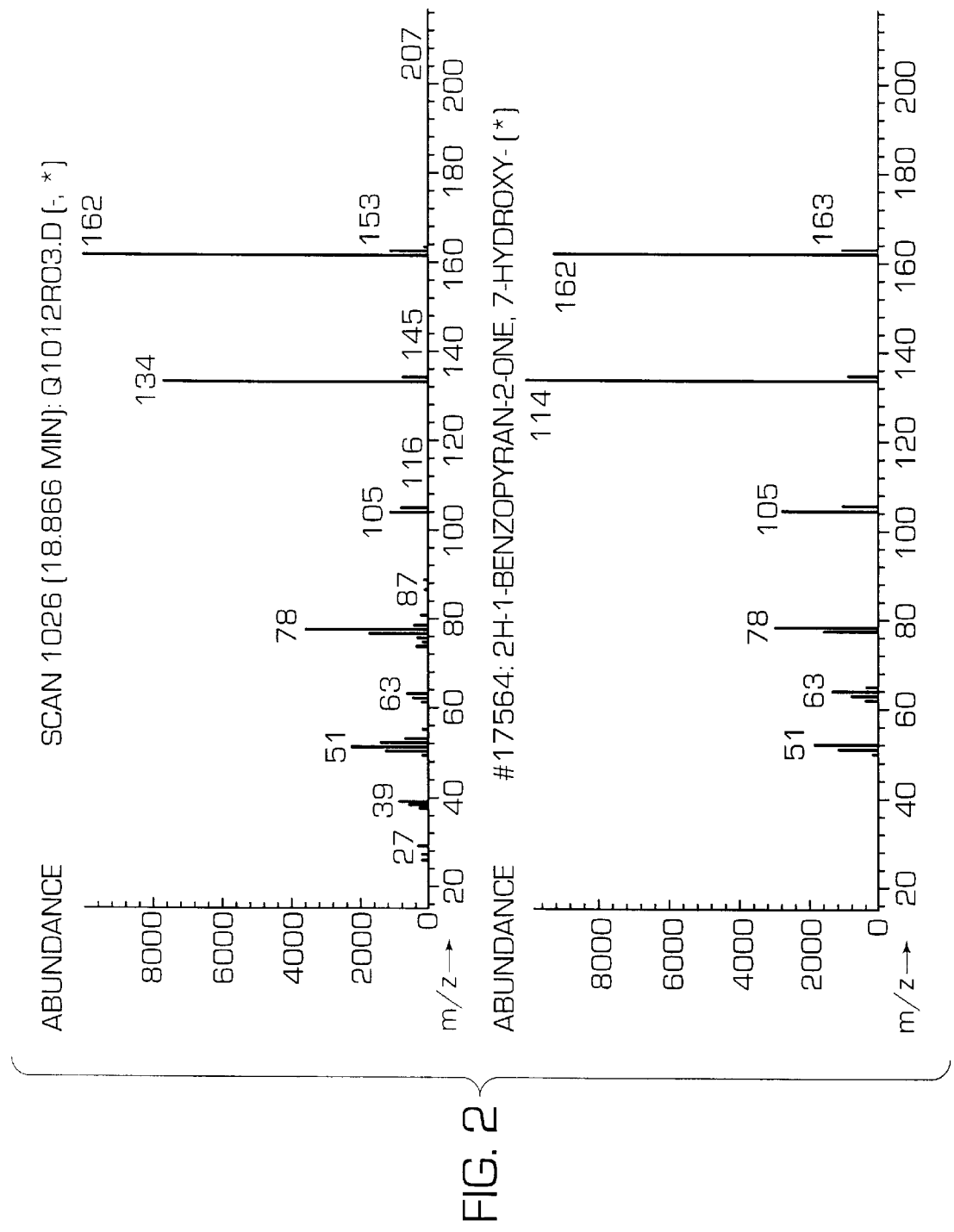
FIG. 2 is a graph which illustrates a comparison of MS data of a metabolite of quinoline produced by *Pseudomonas ayucida* ATCC N° PTA-806 with 7-hydroxy-2H-1-benzopyran-2-one (7-hydroxycoumarin).

Gas Chromatography/Mass Spectroscopy (GC/MS) analysis may be further performed on extracts derived from growing cell as well as resting cells of *Pseudomonas ayucida* PTA-806, allowing for the possible detection of metabolites that do not yield detectable spots in TLC. Two compounds may be identified as metabolites of quinoline produced by *Pseudomonas ayucida* PTA-806: 2-quinolinone and 8-hydroxycoumarin. MS data comparing these metabolites with authentic 2-quinolinone and 7-hydroxycoumarin (7-hydroxy-2H-1-benzopyran-2-one) are shown in FIGS. 1 and 2 respectively.

GC/MS may be used to further analyze the metabolites of quinoline produced by *Pseudomonas ayucida* ATCC N° PTA-806, the relative abundance of these two metabolites being quantified with resting cells exposed to quinoline for various times. The results are shown in TABLE 1 below.

TABLE 1

| Metabolite | 15 min. | 60 min. | 4 hours |
|---|---|---|---|
| 2-quinolinone | 47.8% | 37.3% | 17.2% |
| 8-hydroxycoumarin | 8.4% | 17.3% | 16.7% |

The data set forth in Table 1 are expressed as a percentage of the total area of all peaks present in the chromatograph (with the exception of quinoline). These data strongly indicate that quinoline is first converted to 2-quinolinone and then to 8-hdyroxycoumarin, with other intermediate metabolites as well. FIG. 3 attached illustrates the structures of 2-quinolinone and 8-hydroxycoumarin, these two compounds constituting a partial pathway for the biotransformation of quinoline by *Pseudomonas ayucida* ATCC N° PTA-806.

The oxygenation of the carbon atom adjacent to the nitrogen atom in quinoline to form 2-quinolinone is consistent with the selective cleavage of C—N bonds in quinoline by. *Pseudomonas ayucida* ATCC N° PTA-806.

Moreover, the results of the substrate range tests which indicate that *Pseudomonas ayucida* ATCC N° PTA-806 can utilize quinoline, 3,4-dihydro-2(1H)-quinolinone, 2,4-quinolinediol, 8-hydroxyquinoline and quinoxaline are also consistent with the partial pathway depicted in FIG. 3.

The fact that 8-hydroxycoumarin contains no nitrogen demonstrates that *Pseudomonas ayucida* ATCC N° PTA-806 is capable of selective removal of nitrogen from quinoline. *Pseudomonas ayucida* ATCC N° PTA-806 does not utilize 8-hydroxycoumarin as a carbon source indicating that this compound is not degraded further by this culture. It is believed that the decreased abundance of 8-hydroxycoumarin after longer incubation times is the result of increasing binding to biomass decreasing the recovery efficiency for this compound in analytical procedures.

Contrary to many quinoline-degrading microorganisms which produce pink, green and brown metabolites, *Pseudomonas ayucida* ATCC N° PTA-806 produces no colored metabolites.

Therefore, the researches conducted by the Applicant demonstrate that the pure culture of the *Pseudomonas ayucida* ATCC N° PTA-806 of the invention has two unique, patentably distinguishing features:

The inability to use quinoline as a carbon source;

The selective cleavage of C—N bonds in quinoline and related organonitrogen compounds.

The present invention will now be illustrated by a specific example, which should not be construed as limiting the invention.

EXAMPLE

A petroleum biodenitrogenation test according to the principles of the invention demonstrates the ability of *Pseudomonas ayucida* ATCC N° PTA-806 to remove nitrogen from shale oil. *Pseudomonas ayucida* ATCC N° PTA-806 was grown as described hereinbefore, using quinoline as a sole nitrogen source. Then duplicate washed concentrated cell suspensions were incubated with shale oil samples for 16 hours at 30° C. The control sample consisted of shale oil added to sterile ModA medium which was incubated for 16 hours at 30° C. After incubation the petroleum samples were recovered and analyzed. The results are listed in TABLE 2 below which indicate that pre-grown *Pseudomonas ayucida* ATCC N° PTA-806 cells are capable of removing about 5% of the total organic nitrogen and about 68% of quinoline from shale oil during an overnight (16 hour) incubation. Results in Table 2 are reported as a percentage of the neat oil, except for the amount of quinoline which is reported as the area under the peak corresponding to the retention time of quinoline in gas chromatographs.

TABLE 2

| Element | Control Oil | Biotreated Oil n° 1 | Biotreated Oil n° 2 |
|---|---|---|---|
| Carbon, wt % | 85.01 | 85.21 | 84.87 |
| Hydrogen, wt % | 9.69 | 9.81 | 9.81 |
| Nitrogen, wt % | 1.71 | 1.63 | 1.62 |
| Sulfur, wt % | 1.41 | 1.34 | 1.36 |
| Quinoline (GC peak area) | 177,495 | 58,502 | 57,415 |

Data in Table 2 demonstrate therefore that total nitrogen in petroleum may be reduced in 5% as a result of the exposure of the petroleum oil to the pure culture of the invention. Moreover, about 68% of the quinoline present in petroleum may be removed as a consequence of the biotreatment and therefore biorefining processes for the selective removal of nitrogen from petroleum may be achieved in the presence of biocatalysts such as the *Pseudomonas ayucida* ATCC N° PTA-806 of the invention.

Derivatives of *Pseudomonas ayucida* ATCC No. have been selected which have improved ability to utilize quinoxoline as a sole nitrogen source. This derivative culture retains its ability to selectively cleave C—N bonds in quinoline and has an increased substrate range for the metabolism of additional organonitrogen compounds such as quinazoline and isoquinoline. Similarly, derivatives of *Pseudomonas ayucida* ATCC N° PTA-806 that are resistant to antiobiotics, either by the isolation of chromosomal mutations or by the introduction of suitable plasmids, retain the ability to selectively cleave C—N bonds in quinoline and other organonitrogen compounds. Such property renders *Pseudomonas ayucida* ATCC N° PTA-806 and its derivatives a specific agent for use in organic chemical synthesis for cleavage of organic C—N bonding which may be used in various organic process synthesis systems. Likewise, the unique properties of *Pseudomonas ayucida* ATCC N° PTA-806 and its derivatives that possess the ability to selectively cleave C—N bonds may be utilized in denitrogenating degradation of a wide variety of organic materials.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

What is claimed is:

1. A biologically pure culture of derivative microorganisms of *Pseudomonas ayucida* ATCC N° PTA-806 which has the ability to selectively reduce the nitrogen content of nitrogen-containing organic carbonaceous material by cleavage of organic C—N bonds and production of 8-hydroxycoumarin when grown in a growth medium comprising mineral nutrients and an assimilable source of carbon in the substantial absence of a nitrogen-containing compound except said nitrogen-containing organic carbonaceous material, and in the presence of oxygen at temperatures about 25° C. to 35° C.

2. A biologically pure culture of derivative microorganisms of *Pseudomonas ayucida* ATCC N° PTA-806 which has the ability to selectively reduce the nitrogen content of nitrogen-containing organic carbonaceous material by cleavage of organic C—N bonds by exposing intact bacterial cells, cell extracts, or purified C—N bond cleaving enzyme to carbonaceous nitrogen-containing organic matter at temperatures of from 15 to 40° C. in the presence of oxygen.

* * * * *